US011091455B2

(12) United States Patent
Changoer et al.

(10) Patent No.: US 11,091,455 B2
(45) Date of Patent: *Aug. 17, 2021

(54) PROCESS TO EXTRACT AND PURIFY DELTA-9-TETRAHYDROCANNABINOL

(71) Applicant: APIRx Pharmaceutical USA, LLC, New York, NY (US)

(72) Inventors: Lekhram Changoer, Ridderkerk (NL); Cornelis Herman Michel Van Der Loo, Groningen (NL); Erik Keller, Adorp (NL)

(73) Assignee: APIRx Pharmaceutical USA, LLC, New York, NY (US)

( * ) Notice: Subject to any disclaimer, the term of this patent is extended or adjusted under 35 U.S.C. 154(b) by 18 days.

This patent is subject to a terminal disclaimer.

(21) Appl. No.: 16/774,959

(22) Filed: Jan. 28, 2020

(65) Prior Publication Data
US 2020/0165219 A1 May 28, 2020

Related U.S. Application Data

(63) Continuation of application No. 16/272,817, filed on Feb. 11, 2019, now abandoned, which is a continuation of application No. 16/052,150, filed on Aug. 1, 2018, now Pat. No. 10,246,431, which is a continuation of application No. 15/146,668, filed on May 4, 2016, now Pat. No. 10,059,684.

(60) Provisional application No. 62/158,075, filed on May 7, 2015.

(51) Int. Cl.
*A61K 36/00* (2006.01)
*C07D 311/80* (2006.01)
*B01D 11/02* (2006.01)

(52) U.S. Cl.
CPC ........ *C07D 311/80* (2013.01); *B01D 11/0288* (2013.01)

(58) Field of Classification Search
CPC ..................................................... A61K 36/00
USPC ....................................................... 424/725
See application file for complete search history.

(56) References Cited

U.S. PATENT DOCUMENTS 7,592,488 B2 * 9/2009 Kim ...................... C07C 217/58
549/404

* cited by examiner

*Primary Examiner* — Michael V Meller
(74) *Attorney, Agent, or Firm* — Swidler Law Group, LLC; Sean S. Swidler

(57) ABSTRACT

$\Delta^9$-THC carboxylic acid is extracted from *cannabis* flowers using a first organic solvent, then separated using a second aqueous solvent. $\Delta^9$-THC carboxylic acid is converted to $\Delta^9$-THC carboxylic salt before being extracted by a third organic solvent and converted back to $\Delta^9$-THC carboxylic acid. Using a solvent swap, $\Delta^9$-THC carboxylic acid is decarboxylated and extracted again with an organic solvent prior to purification to give $\Delta^9$-THC.

11 Claims, 6 Drawing Sheets

FIG. 1. Delta-9-THC acid extraction

FIG. 2. Delta-9-THC production

PROCESS TO EXTRACT AND PURIFY DELTA-9-TETRAHYDROCANNABINOL

CROSS-REFERENCE TO RELATED APPLICATIONS

This application is a continuation of U.S. application Ser. No. 16/272,817, filed Feb. 11, 2019, which is a continuation of U.S. application Ser. No. 16/052,150, filed Aug. 1, 2018, now U.S. Pat. No. 10,246,431, which is a continuation of U.S. application Ser. No. 15/146,668, filed May 4, 2016, now U.S. Pat. No. 10,059,684, which claims the benefit of U.S. Provisional Application No. 62/158,075, filed May 7, 2015. Each of the above-referenced patent applications is incorporated by reference in its entirety.

BACKGROUND OF THE INVENTION

Field of the Invention

The present invention relates to a process to extract $\Delta^9$-tetrahydrocannabinol carboxylic acid ($\Delta^9$-THC-A) from the plant *Cannabis sativa* L., to decarboxylate $\Delta^9$-tetrahydrocannabinol carboxylic acid to obtain $\Delta^9$-THC, and a process to purify $\Delta^9$-THC without the use of a reverse phase column.

Description of the Related Technology

The *cannabis* plant has many naturally occurring substances that are of great interest in the fields of science and medicine. Cannabinoids are a family of naturally occurring $C_{21}$ terpenophenolic compounds uniquely produced in *cannabis* plants. There are a total of eighty-five (85) cannabinoids that have been isolated from the *cannabis* plant. Many researchers have confirmed the medicinal value of cannabinoids. Cannabinoids have been investigated for possible treatment of seizures, nausea, vomiting, lack of appetite, pain, arthritis, inflammation, and other conditions.

Isolated cannabinoids from the *cannabis* plant include tetrahydrocannabinol (THC), cannabidiol (CBD), cannabichromene (CBC), cannabigerol (CBG), cannabidivarin (CBDV), among other compounds. While THC has psychoactive effects, CBD, CBC, CBG, and CBDV do not. THCs contain two main isomeric forms, $\Delta^9$-tetrahydrocannabinol and $\Delta^8$-tetrahydrocannabinol, depending on the position of the double bond.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((2S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. These are among the most prominent compounds in the family of compounds extracted from the *cannabis* plant referred to as cannabinoids.

In the *cannabis* plant, THC is present in carboxylic acid form. The major component of the *cannabis* plant is $\Delta^9$-THC-A, which exists in two isomeric forms, $\Delta^9$-THC-A-A and $\Delta^9$-THC-A-B, both of which are psychomimetically inactive. Decarboxylation of these isomeric $\Delta^9$-THC-A converts them into the psychomimetically active form, $\Delta^9$-THC. Decarboxylation is process that happens either slowly in storage, or quickly by heat application.

SUMMARY

This invention relates to a method to extract THC-A from *cannabis* flower using a non-polar solvent, wherein the yield is approximately 50-70% with regards to THC-A content in the starting material. A neutral metal salt/inorganic base solution saturated with the metal neutral salt and adjusted to pH 13.2-13.4 enables easy separation of the THC-A layer and increases the yield. THC-A is decarboxylated in a water/ethanol solution to give THC at a purity of 92-94%. The overall yield THC is approximately 40-55% of the THC-A content in the starting material.

Abbreviations

CBC: Cannabichromene
CBD: Cannabidiol
CBDV: Cannabidivarin
CBG: Cannabigerol
CBN: Cannabinol
$\Delta^9$-THC: delta-9-tetrahydrocannabinol
$\Delta^9$-THC-A: delta-9-tetrahydrocannabinolic acid/delta-9-tetrahydrocannabinol carboxylic acid
H-NMR: Proton nuclear magnetic resonance
g: Gram
IUPAC: International Union of Pure and Applied Chemistry
L: Liter
LC/MS: Liquid chromatography-mass spectrometry
mL: Milliliter
TBME: tert-butyl methyl ether
THC: Tetrahydrocannabinol
THC-A: Tetrahydrocannabinolic acid/tetrahydrocannabinol carboxylic acid
wt: weight

DETAILED DESCRIPTION OF CERTAIN INVENTIVE EMBODIMENTS

Figure 1:
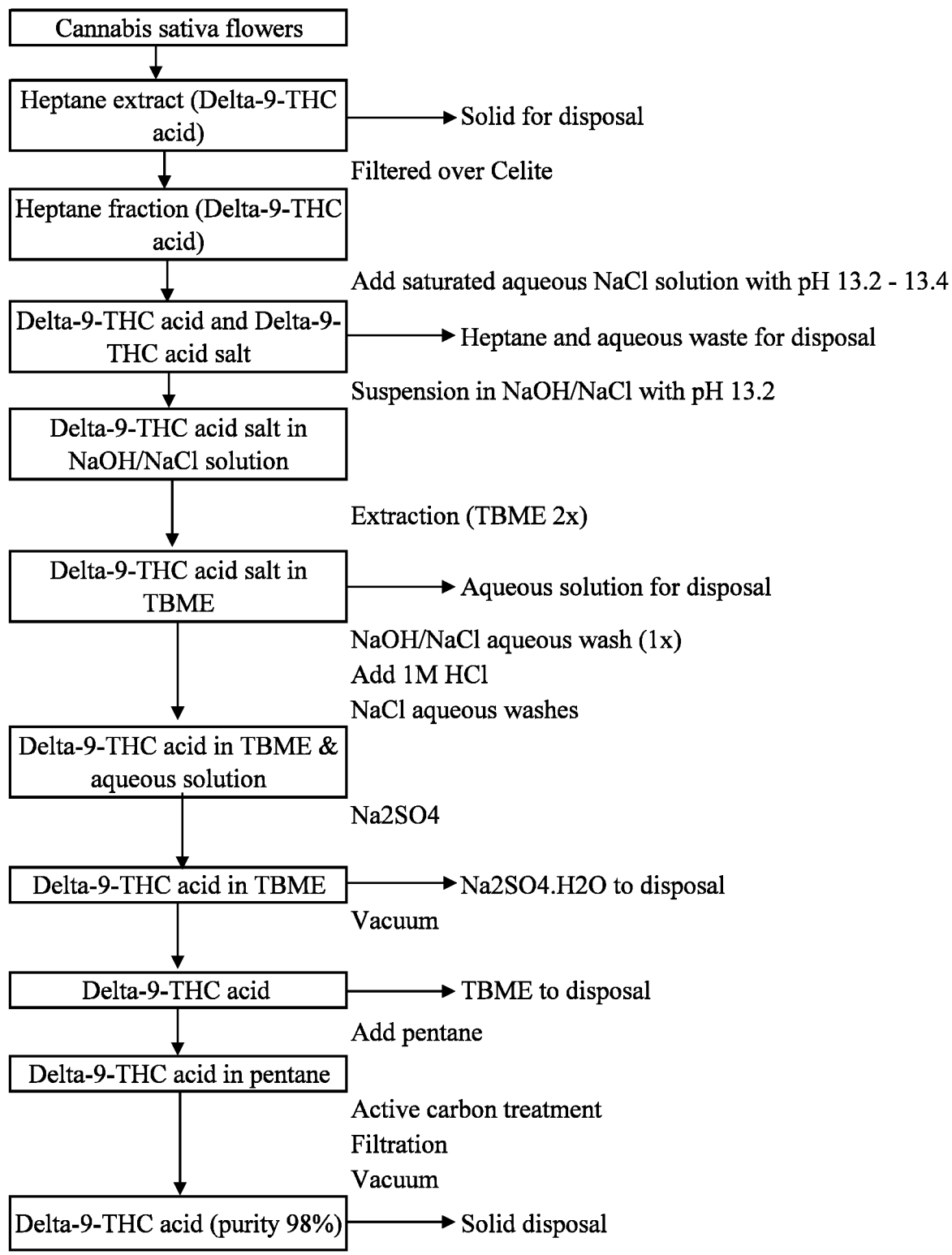
FIG. 1 is the flowchart of the $\Delta^9$-THC carboxylic acid extraction process from *cannabis* flower according to embodiments.
Figure 2:
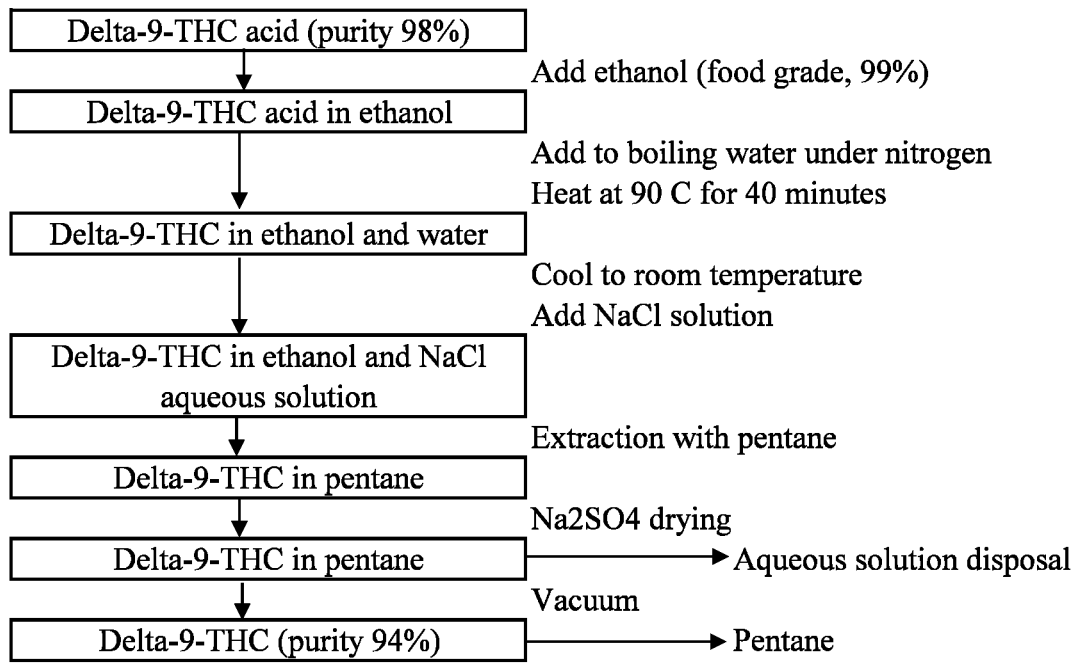
FIG. 2 is the flowchart of the $\Delta^9$-THC carboxylic acid decarboxylation process to produce $\Delta^9$-THC according to embodiments.
Figure 3:
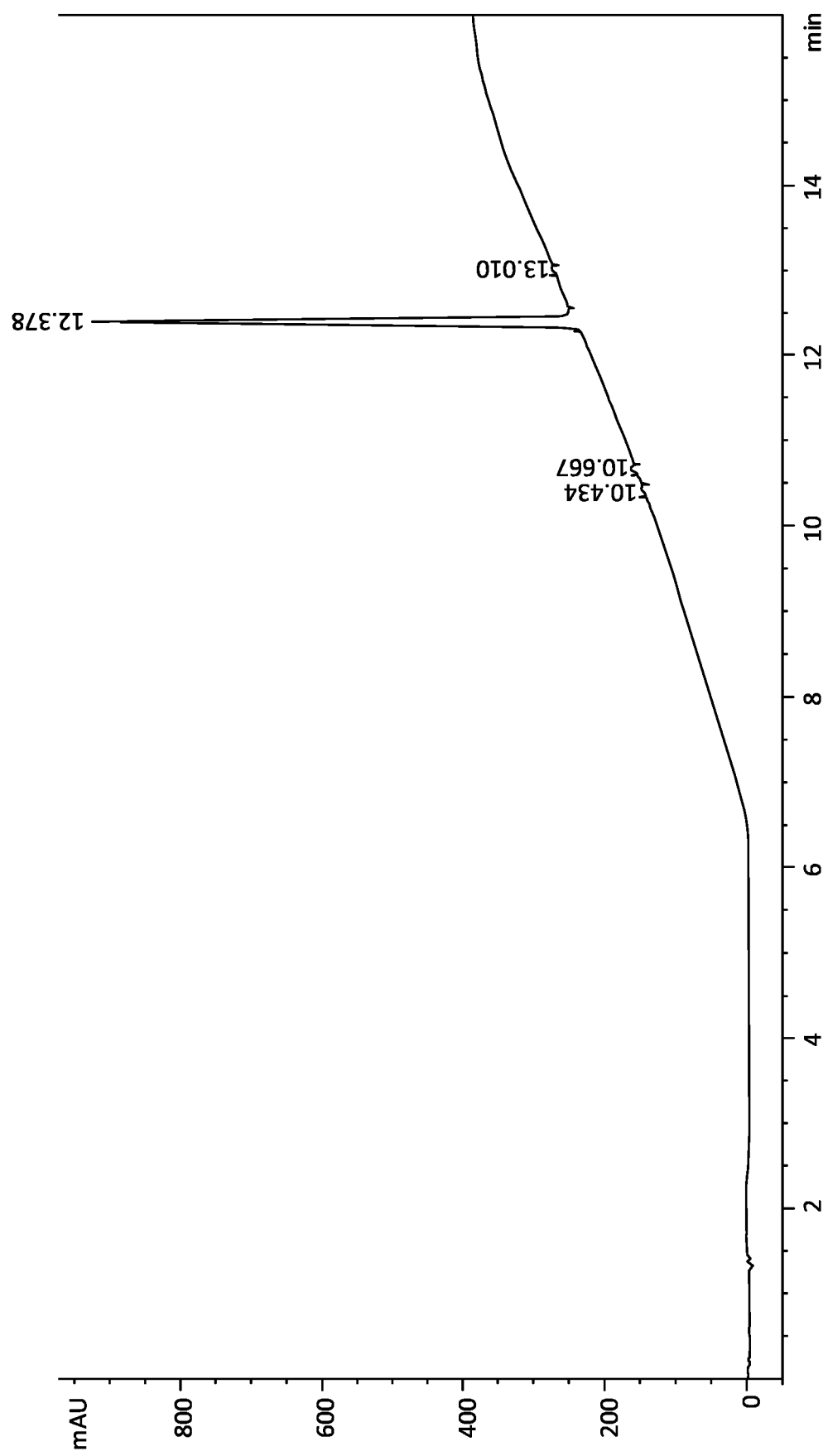
FIG. 3 is the representative LC/MS data of the $\Delta^9$-THC carboxylic acid yield from the process represented in FIG. 1 according to embodiments.
Figure 4:
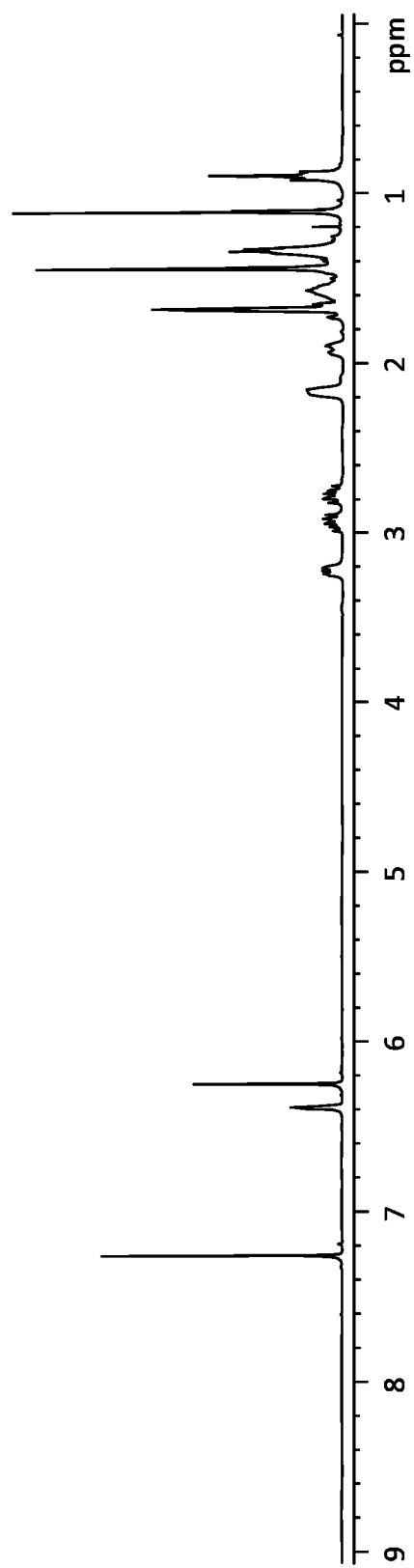
FIG. 4 is the representative H-NMR data of the $\Delta^9$-THC carboxylic acid yield from the process represented in FIG. 1 according to embodiments.
Figure 5:
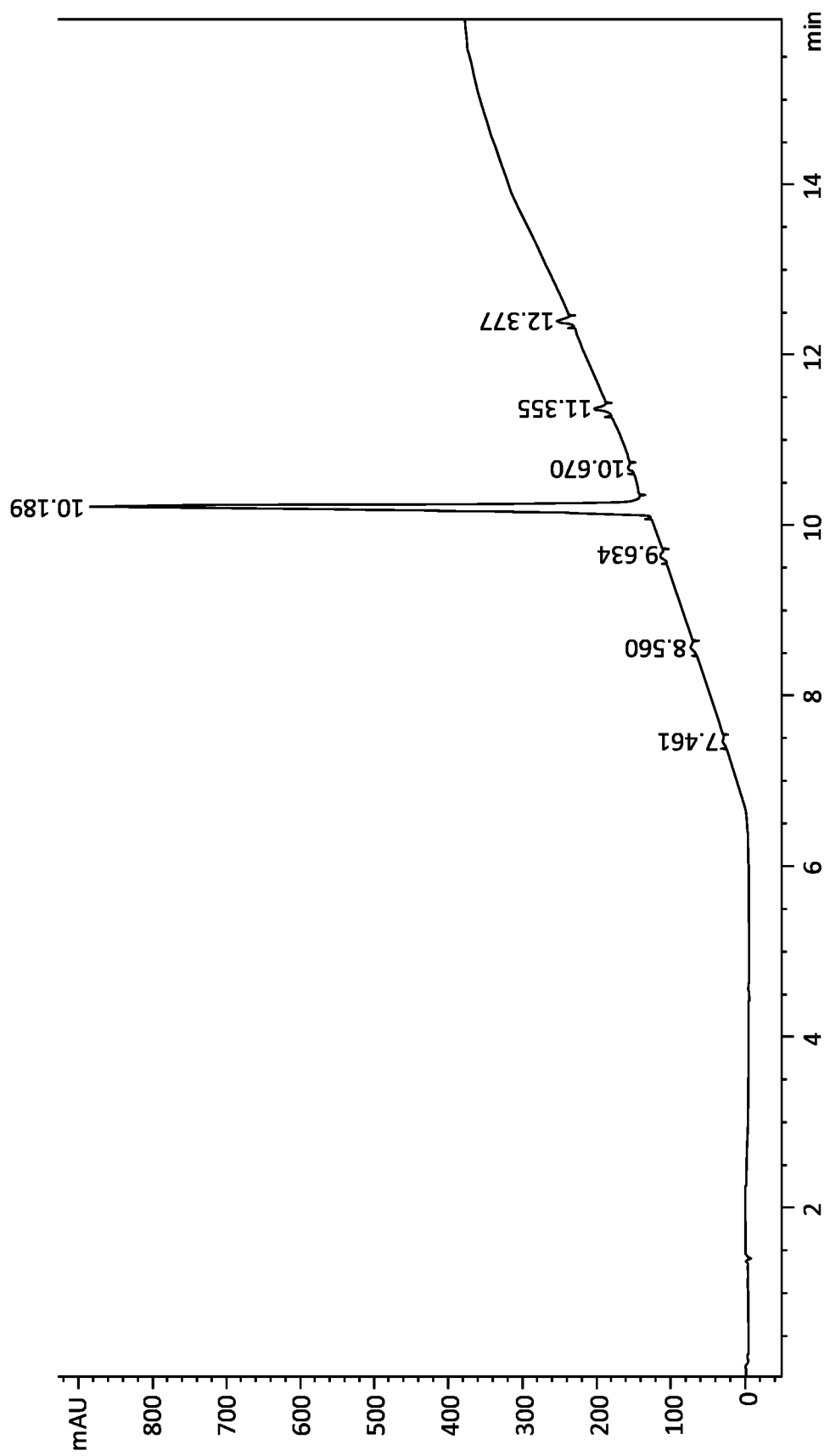
FIG. 5 is the representative LC/MS data of the $\Delta^9$-THC yield from the process represented in FIG. 2 according to embodiments.
Figure 6:
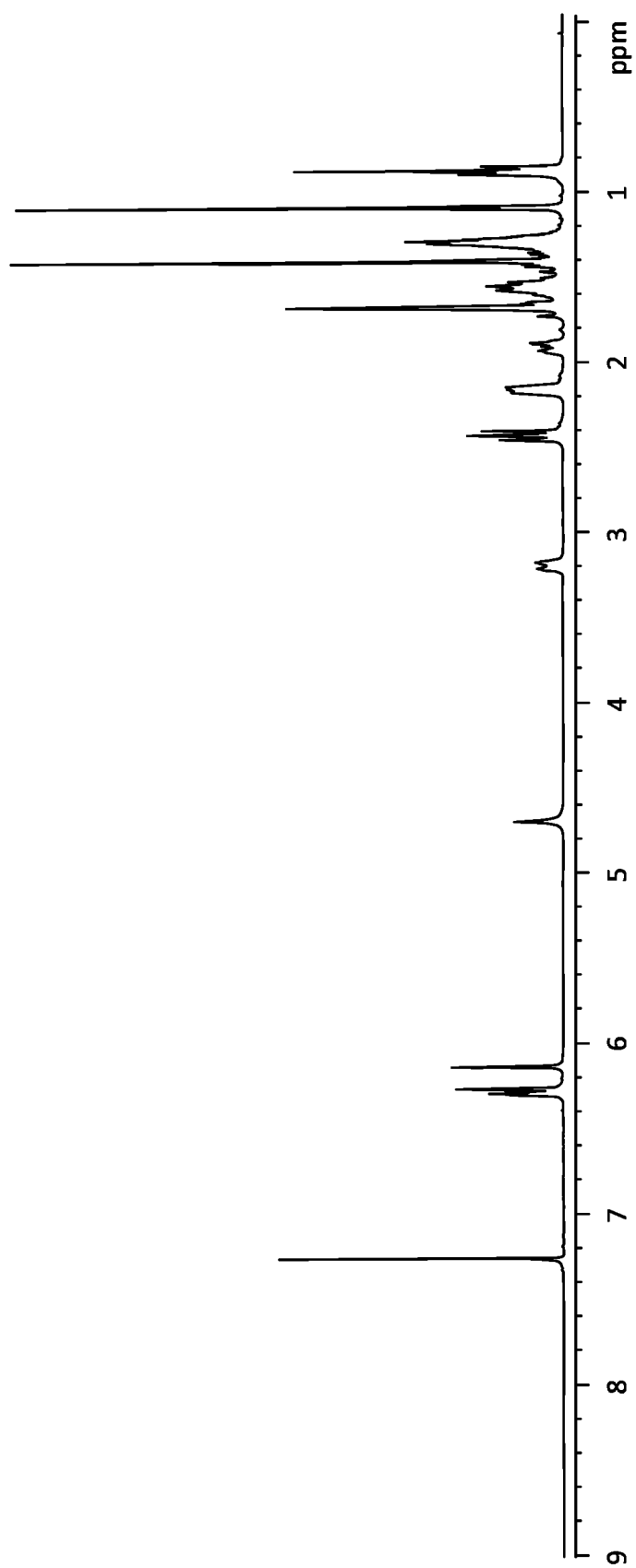
FIG. 6 is the representative H-NMR data of the $\Delta^9$-THC yield from the process represented in FIG. 2 according to embodiments.

This present invention is capable of being embodied in various forms. The description below of several embodiments is made with the understanding that the present disclosure is to be considered as an exemplification of the claimed subject matter, and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in their non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more."

The word "THC" denotes (−)-trans-$\Delta^9$-tetrahydrocannabinol ((6aR,10aR)-delta-9-tetrahydrocannabinol), having a IUPAC name of (−)-(6aR,10aR)-6,6,9-Trimethyl-3-pentyl-6a,7,8,10a-tetrahydro-6H-benzo[c]chromen-1-ol. In this application, $\Delta^9$-THC and THC may be used interchangeably.

The word "THC-A" denotes tetrahydrocannabinolic acid, having a IUPAC name of (6aR,10aR)-1-hydroxy-6,6,9-trimethyl-3-pentyl-6a,7,8,10a-tetrahydro-6h-b enzo[c] chromene-2-carboxylic acid. In this application, $\Delta^9$-THC-A and THC-A may be used interchangeably.

The present invention relates to a method to extract THC-A from *cannabis* plant material and to produce THC from the extracted THC-A is provided. In the first aspect of the invention, THC-A may be extracted from the *cannabis* plant material, in particular from *cannabis* flowers, using a non-polar organic solvent or a mixture of non-polar organic solvents, then filtered over Celite to remove plant material, before the non-polar solvent extract is placed in contact with an aqueous phase saturated with a metal neutral salt. The aqueous phase is adjusted to pH 13.2-13.4 using a base having the same metal salt with the neutral metal salt. The extract may form a 3-layer system, comprising an organic solvent layer, an oil layer containing THC-A and THC-metal salt, and an aqueous layer.

Solvents suitable for the first extraction step may be an organic solvent, such as a non-polar solvent or a mixture of non-polar solvents, including straight or branched alkanes, or C4-C9 alkane, in particular pentane, hexane, heptane, octane, or nonane. Other non-polar solvents immiscible with water may also be used. Polar solvents, such as ethanol, may extract other plant materials such as flavonoids, waxes, and terpenes, which may further complicate the purification process.

An advantage of this method is to increase yield of THC-A from the starting material (*cannabis* flowers). By providing an aqueous solvent saturated with a neutral metal salt and adjusted to pH 13.2-13.4 using a base with the same metal as the neutral metal salt, the organic solvent used in the first extraction step may be separated from the oil layer, which comprises the main extracts from the *cannabis* flowers, and an aqueous layer at the bottom. The pH level also may increase conversion of THC-A into THC-metal salt while preventing degradation of THC-A. After discarding the organic solvent layer and the aqueous layer, the oil layer has both THC-A and THC-metal salt and may be extracted again thereafter.

By using a saturated neutral metal salt solvent with pH adjusted to 13.2-13.4, more THC-A and THC-metal salt may be recovered from this process, giving a higher yield of THC in the end. THC-metal salt may remain in the oil layer since the aqueous solvent is saturated with the metal salt. The first layer may be the organic solvent layer with dissolved THC-A in it, but THC-A may be mainly present in the oily layer. The third layer may be the aqueous layer with little THC-metal salt, as it may be saturated by the neutral metal salt.

The oily layer may be further converted into THC-metal salt by contact with an aqueous phase at high pH (13.2-13.4) saturated with dissolved metal salt. After further extraction steps with a different non-polar solvent, such as an ether, in particular tert-butyl methyl ether, and conversion back into THC-A using an acidic solution, with excess acid removed by a contact with a base. Water and the organic non-polar solvent may be removed to enable the purification process, yielding THC-A at 55-70% with respect to THC-A content in *cannabis* flower, or 10-15% with respect to *cannabis* flower weight.

Decarboxylation may be carried out in a polar solvent in the presence of water at 80° C.-100° C. for less than 1 hour. The advantage of this decarboxylation process may be shorter time and with less energy expended. The decarboxylated mixture may be once again extracted with the non-polar solvent, and the non-polar solvent may be removed to give THC.

After decarboxylation, the mixture may be extracted again with a non-polar to separate THC from the mixture. The advantage of this step may be the easy removal of the non-polar solvent, such as n-pentane, and separation of THC at an acceptable purity.

In use of the invention, *cannabis* flowers may be immersed in a first organic solvent, such as heptane or a C4-C9 alkane solvent, to produce an extract. Immediately after the first organic solvent extraction, the extract may be filtered, for example over Celite, to remove any solid plant matter from the extract, giving a solvent extract containing THC-A. The second extraction in an aqueous solution may start with preparation of the aqueous solution. Water may be saturated with a metal salt, such as sodium chloride (NaCl), but can also be $MgCl_2$, KCl, or LiCl, and the pH of the aqueous solution is adjusted to 13.2-13.4 using a base having the same metal with the neutral metal salt. For example, an aqueous solution saturated with NaCl may be adjusted to pH 13.2-13.4 using NaOH.

This pH range may provide 2-fold benefits: the pH level may be low enough to prevent degradation and decarboxylation of THC-A, while at the same time may enable adequate extraction of THC-A. Saturation of the aqueous solution with a neutral metal salt may prevent emulsion but at the same time may prevent THC-A from dissolving in the aqueous phase, resulting in THC-A present in the oily phase between the organic layer and the aqueous phase.

Adding an aqueous solvent saturated with a neutral metal salt, such as a NaOH/NaCl solution saturated with NaCl, may ensure that THC-metal salt remains in the oily phase, which also contains not-converted THC-A. The presence of the aqueous phase saturated with NaCl not only may reduce emulsion and thus remove THC-A and THC-metal salt presence in the aqueous phase, but also may cause THC-A and THC-metal salt to stay in the oily phase. This in turn may increase THC-A yield from *cannabis* flowers. Typically, this method may yield crude THC-A at 10-15% efficiency from the starting plant material.

By using an aqueous solution saturated with a dissolvable metal salt, the extracted mixture may separate into three layers. The top layer may be the organic solvent, the middle layer may be the oil extracted from the plant material, and the bottom layer may be the aqueous solution. The top and bottom layers may be discarded, leaving the oily middle layer, where THC-A and THC-metal salt are located. Depending on the aqueous solution saturated with NaCl, $MgCl_2$, KCl, or LiCl and having NaOH, $Mg(OH)_2$, KOH, or LiOH, the THC-metal salt may be sodium, magnesium, potassium, or lithium salt.

The use of the saturated aqueous phase may also reduce THC-A dissolution in the aqueous phase. Separation of the phases may be by a separatory funnel with a valve at the bottom. The use of heptane and strict control of pH levels in washing and separation may allow easy isolation of the oily layer, which contains THC-A.

In another aspect of this invention, the oily layer isolated from the step above may be suspended in a salt/alkali solution, such as a NaOH/NaCl solution, adjusted to pH 13.2-13.4 using a base having the same metal with the neutral metal salt. THC-metal salt may be formed from THC-A present in the oil layer after contact with the base in the solution. This is in addition to the THC-metal salt already formed in the previous step. Once THC-A is converted to THC-metal salt, THC-metal salt may be extracted with another organic solvent, such as an ether, more specifically, tert-butyl methyl ether, for up to 2 times. This extraction may give an ether solution with THC metal salt separated from an aqueous layer. The aqueous layer may be discarded, giving an ether solution with THC metal salt for further processing.

THC-metal salt in the third solvent, such as an ether solvent, may be converted back to THC-A using an inorganic, strong acid. The reaction between THC-metal salt and the inorganic acid may give THC-A and a neutral metal salt, resulting in THC-A in the ether solvent. Excess inorganic acid may be neutralized with a basic solution containing a neutral metal salt, such as a NaOH/NaCl solution. The THC-A in ether solvent may go through various purifying steps, including drying with $Na_2SO_4$, removal of the third organic solvent, dissolution in another non-polar solvent such as pentane, treatment with active carbon to remove other cannabinoids, removal of the non-polar solvent by vacuum, and filtration to yield THC-A solid.

THC-A may be converted to THC in a decarboxylation process. Decarboxylation may happen in a different solvent, such as an alcohol, which may achieve decarboxylation at a lower temperature and much less time. Suitable alcohols may be ethanol, isopropyl alcohol, propyl alcohol, or butyl alcohol. To prevent oxidation, THC-A may be dissolved in the solvent under an inert gas, such as nitrogen, argon, or helium. Decarboxylation may be carried out by heat, with the advantage of low heat application, usually less than 100° C. and for a short amount of time, such as less than 60 minutes. Heat application may be between 80° C.-100° C. for at least 40 minutes.

After decarboxylation, THC may be extracted again using an aqueous solvent enhanced with metal salt to separate THC (hydrophobic) before THC is extracted into a non-polar solvent, such as an alkane. The final THC in non-polar solvent mixture may be dried, before the non-polar solvent is removed by heat and vacuum pressure application. THC harvested from this process may be of high purity.

In the extraction process according to embodiments, THC-A may be extracted and converted to THC in a multi-step process. *Cannabis sativa* L. flower in whole may be extracted with heptane in an open vessel for 1 hour. Extraction of whole flowers may allow high purity THC at the end of the process, as THC-A present in the trichomes may be extracted without other cannabinoids and/or plant materials mixed in. The heptane extract may be filtered over Celite to remove any solid plant matters. The heptane extract now may contain THC-A and other minor cannabinoids mixed in.

An aqueous solution adjusted to pH 13.2-13.4 with NaOH may be saturated with NaCl and added into the heptane extract. In doing so, some THC-A may be converted to THC sodium salt. The saturated NaCl aqueous solution may minimize suspension of THC-A in the extraction and separate the heptane/aqueous extract mixture into three layers: heptane, oil (with THC-A and THC sodium salt), and aqueous solution. The oily layer may be separated, suspended in a NaOH/NaCl solution adjusted to pH 13.2-13.4 and with NaCl concentration at 180 g/L to further convert THC-A into THC sodium salt. The aqueous mixture may be then extracted into tert-butyl methyl ether (TBME), which may dissolve THC-A. The TBME extract may be washed in NaOH/NaCl solution, then acidified (with 1M HCl) to convert THC-sodium salt back to THC-A. Excess acid may be neutralized with an inorganic base to convert to a neutral metal salt. For example, HCl may be neutralized with NaOH to give NaCl, which is dissolved in the aqueous phase.

The TBME/aqueous/THC-A mixture at this point may go through a drying process. First, water may be removed using $Na_2SO_4$. Then, TBME may be removed by a concentrating process using vacuum pressure. The resulting solid, which is crude THC-A, may be dissolved in a non-polar solvent, for example pentane, before active carbon treatment. Active carbon treatment may be more effective in pentane, such that cannabinoids other than THC isomers may be removed. Active carbon may be added and stirred in the mixture for 30 minutes, before the mixture is filtered to remove solid matters, and concentrated under vacuum to remove pentane. The solid is now THC-A at a purity of 98%.

THC-A solid may be dissolved in ethanol and added into boiling water under nitrogen to prevent oxidation. The mixture may be heated to 90° C. for at least 40 minutes to decarboxylate THC-A. The mixture may be cooled down to room temperature and a saturated neutral alkali salt solution, such as NaCl solution, may be added to further separate the oily phase from the water phase. The mixture may be extracted with pentane up to 3 times, before water is dried out of the mixture using $Na_2SO_4$. Pentane may be removed by vacuum application and heat application at 50° C., yielding crude THC with purity at 92-94%.

THC may then be combined with pharmaceutically acceptable carriers for further processing usage. THC may be combined with, for example, isomalt, to form a mixture that may be used in pharmaceutical products.

EXAMPLES

Example 1

Extraction

Extraction With Heptane Fraction

*Cannabis* flowers from strain Bedrocan, with 22% THC-A by weight percent in *cannabis* flower, are harvested by cutting. Whole *cannabis* flowers (100 g) are placed in an open vessel and suspended in heptane (1.5 L). The content is stirred at room temperature for 60 minutes. The content is then filtered over Celite (50 g) to remove solid materials. Liquid filtrate comprising of heptane fraction, THC-A, and other plant materials is collected.

Aqueous Phase Preparation

NaOH/NaCl solution adjusted to pH 13.2-13.4 with NaOH and saturated with NaCl is prepared. This solution is added to water and gently stirred, then pH level is tested.

More NaOH solution (10M) may be added to adjust pH level until it reaches 13.2-13.4. NaCl is added to reach 180 g/L concentration.

Aqueous Phase Extraction

The heptane extract is extracted with the NaOH/NaCl solution as prepared above. The NaOH/NaCl solution is added into the vessel where the heptane extract sits. The content is stirred at ambient temperature for 10 minutes and then allowed to settle. The first wash results in a 3-layer system, and the lower aqueous layer is discarded using a separatory funnel with a valve at the bottom. The second wash results in a 3-layer system and the lower aqueous layer is again discarded. The third wash results in a 3-layer system, with THC-A separated from the heptane phase forming a middle layer.

The liquid in the vessel now forms a 3-layer system. The first layer is heptane, the second layer is an oily layer, and the third layer is an aqueous solution. The second, oily layer is isolated, while the first and third layers are discarded. Separation is by a separatory funnel with a control valve at the bottom. The oily THC-A layer is collected and kept for further processing. The oily layer is then suspended in NaOH/NaCl solution (pH 13.2, NaCl 180 g/L).

Solvent Extraction

The oil/water suspension is extracted with TBME (200 mL, 2 times). The combined TBME extract is washed with NaOH/NaCl solution (pH=13.2, NaCl concentration 180 mg/L) once, then acidified with HCl (1 M) twice (200 mL each time). The TBME extract is then washed with saturated NaCl solution (100 mL). The mixture now separates into 2 layers: the TBME organic layer and the aqueous layer. The TBME layer is separated and dried on sodium sulfate ($Na_2SO_4$, 25 g).

Batch Concentration

The combined TBME extract is concentrated under vacuum (Rotavap) at 50° C., giving a light brown foam (14.4 g). This yield is approximately 14.4% with respect to the *cannabis* flower, or approximately 65% of THC-A is extracted.

Charcoal Treatment/Solvent Swap

The brown foam from above is dissolved in n-pentane (140 mL). Active carbon (10% wt, 1.4 g) is added into the mixture and stirred for 30 minutes. The mixture is then filtered over paper filter to remove solid matter, with the heptane fraction collected. The heptane fraction is then concentrated under vacuum at 50° C. to remove heptane, yielding THC-A (11.8 g) at a purity of approximately 97-99%. THC-A yield at this point is 54% with regards to the initial THC-A content in *cannabis* flower, and is 11.8% with regards to *cannabis* flower weight.

Decarboxylation

In a vessel, THC-A (11.8 g) is dissolved in ethanol (food grade, 99%, 175 mL) and stirred. In another heated vessel, water (990 mL) is boiled and bubbling under nitrogen. The ethanol/THC-A solution is added to boiling water and the temperature is maintained at 90-91° C. for 30-40 minutes to reflux, then allowed to cool down to room temperature.

Example 2

Purification n-Pentane Extraction

After heating, THC-A in ethanol is decarboxylated to THC. Add NaCl solution (saturated, 500 mL) to the cool ethanol/THC mixture. The mixture is extracted with n-pentane 3 times (300 mL each time).

Drying and Concentration

The combined n-pentane extract is then dried with sodium sulfate ($Na_2SO_4$, 20 g). The n-pentane combined extract is then concentrated under vacuum at 50° C. to remove n-pentane from the mixture, yielding THC (10.3 g) at purity approximately 92-94%.

Results

THC yielded from this method has approximately 92-94% in purity, and the yield is 10-15% with respect to the *cannabis* flower weight.

All references, including publications, patent applications, and patents, cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

What is claimed is:

1. A method of producing $\Delta^9$-THC consisting essentially of:
   extracting $\Delta^9$-THC carboxylic acid from *cannabis* flowers using heptane to obtain a heptane extract;
   filtering the heptane extract to remove solid plant matter;
   separating the $\Delta^9$-THC carboxylic acid from the heptane extract by contacting the heptane extract with sodium chloride water adjusted to a pH range of 13.2 to 13.4 using an inorganic base to form a liquid mixture;
   stirring the liquid mixture; and
   leaving the liquid mixture to settle;
   wherein the liquid mixture forms three layers consisting of a first organic layer, a second oily layer, and third aqueous layer; and
separating out the oily layer from the other two layers by a separatory funnel to yield $\Delta^9$-THC.

2. The method of claim 1, further consisting essentially of suspending the oily layer in an aqueous solvent consisting essentially of sodium chloride and an inorganic base to adjust the aqueous solvent to a pH of 13.2 to 13.4 to convert $\Delta^9$-THC carboxylic acid to $\Delta^9$-THC carboxylic salt.

3. The method of claim 2, further consisting essentially of extracting $\Delta^9$-THC carboxylic salt with an organic solvent.

4. The method of claim 3, wherein the organic solvent is tert-butyl methyl ether.

5. The method of claim 3, further consisting essentially of converting the $\Delta^9$-THC carboxylic acid salt in the organic solvent back to $\Delta^9$-THC carboxylic acid by adding an aqueous solvent consisting essentially of sodium chloride and an inorganic base to adjust the aqueous solvent to a pH of 13.2 to 13.4 and a strong inorganic acid into the $\Delta^9$-THC carboxylic salt in organic solvent mixture.

6. The method of claim 5, further consisting essentially of:
   washing the resulting mixture with a sodium chloride water solution to form an organic solvent layer and an aqueous layer; and separating the organic solvent layer from the aqueous layer, wherein the organic solvent layer consists essentially of $\Delta^9$-THC carboxylic acid in water and organic solvent.

7. The method of claim 6, further consisting essentially of:
removing water from the $\Delta^9$-THC carboxylic acid in water and organic solvent mixture using $Na_2SO_4$;
removing the organic solvent using vacuum to give a crude solid consisting essentially of $\Delta^9$-THC carboxylic acid;
dissolving the solid in pentane;
treating the crude solid containing $\Delta^9$-THC carboxylic acid dissolved in pentane with active carbon to remove non-THC cannabinoids;
removing the pentane using vacuum; and
filtering to obtain a $\Delta^9$-THC carboxylic acid solid.

8. The method of claim 7, further consisting essentially of:
dissolving the $\Delta^9$-THC carboxylic acid solid with an alcohol and adding the mixture into boiling water;
heating the mixture to between 80° C. and 100° C. for at least 40 minutes; and
cooling the mixture to room temperature and adding a sodium chloride solution into the mixture;
wherein the $\Delta^9$-THC carboxylic acid is decarboxylated to convert $\Delta^9$-THC carboxylic acid to $\Delta^9$-THC.

9. The method of claim 8, wherein the alcohol is ethanol, isopropyl alcohol, propyl alcohol, or butyl alcohol.

10. The method of claim 8, further consisting essentially of extracting the $\Delta^9$-THC using n-pentane 1 to 3 times.

11. The method of claim 10, further consisting essentially of purifying the $\Delta^9$-THC by removing water using $Na_2SO_4$ and removing n-pentane by a vacuum.

\* \* \* \* \*